US011613733B2

(12) United States Patent
Akazawa et al.

(10) Patent No.: US 11,613,733 B2
(45) Date of Patent: Mar. 28, 2023

(54) METHOD FOR PURIFYING MESENCHYMAL STEM CELLS TO IMPROVE TRANSPLANTATION EFFICIENCY

(71) Applicants: JSR CORPORATION, Tokyo (JP); MEDICAL & BIOLOGICAL LABORATORIES CO., LTD., Tokyo (JP)

(72) Inventors: Chihiro Akazawa, Tokyo (JP); Eriko Grace Suto, Tokyo (JP); Yo Mabuchi, Tokyo (JP)

(73) Assignees: Medical & Biological Laboratories Co., Ltd., Tokyo (JP); JSR Corporation, Tokyo (JP)

( * ) Notice: Subject to any disclaimer, the term of this patent is extended or adjusted under 35 U.S.C. 154(b) by 241 days.

(21) Appl. No.: 16/612,236

(22) PCT Filed: May 11, 2018

(86) PCT No.: PCT/JP2018/018351
§ 371 (c)(1),
(2) Date: Nov. 8, 2019

(87) PCT Pub. No.: WO2018/207918
PCT Pub. Date: Nov. 15, 2018

(65) Prior Publication Data
US 2020/0239849 A1 Jul. 30, 2020

(30) Foreign Application Priority Data

May 12, 2017 (JP) .............................. JP2017-095216

(51) Int. Cl.
*C12N 5/0775* (2010.01)
*A61K 35/28* (2015.01)

(52) U.S. Cl.
CPC ......... *C12N 5/0665* (2013.01); *C12N 5/0663* (2013.01); *C12N 5/0664* (2013.01); *A61K 35/28* (2013.01)

(58) Field of Classification Search
None
See application file for complete search history.

(56) References Cited

U.S. PATENT DOCUMENTS 6,261,549 B1 * 7/2001 Fernandez ........... A61K 38/193
424/85.1
2010/0260721 A1 10/2010 McGonagie et al.
2011/0053183 A1 3/2011 Matsuzaki et al.
2013/0183272 A1 7/2013 Kimbrel et al.
2014/0120542 A1 5/2014 Tlsty
2014/0341863 A1 11/2014 Marasco et al.
2016/0038545 A1 2/2016 Patel et al.
2016/0123980 A1 5/2016 Evans et al.
2017/0335283 A1 * 11/2017 Wang .................... A61K 39/00

FOREIGN PATENT DOCUMENTS

| JP | 2009-060840 A | 3/2009 |
| JP | 2015-500810 A | 1/2015 |
| JP | 2016-513962 A | 5/2016 |
| JP | 2016-519938 A | 7/2016 |
| WO | WO 2007/083093 A1 | 7/2007 |
| WO | WO 2012/100084 A1 | 7/2012 |
| WO | WO 2013/067038 A1 | 5/2013 |

OTHER PUBLICATIONS

Boiret et al. "Characterization of nonexpanded mesenchymal progenitor cells from normal adult human bone marrow", (2005), Experimental Hematology, vol. 33: 219-225. (Year: 2005).*
Boiret et al. "CD34+ CD290(thy-1)+ subset colocated with mesenchymal progenitors in human normal bone marrow hematon units is enriched in colony-forming unit megakaryocytes and long-term culture-initiating cells" (2003), Exp. Hematology, 31: 1275-1283. (Year: 2003).*
Zhu et al. "Stem cell separation technologies" 2013, Current Opinion in Chemical Engineering, vol. 2: 3-7 (Year: 2013).*
Carrancio S. et al., Effects of MSC Coadministration and Route of Delivery on Cord Blood Hematopoietic Stem Cell Engraftment., Cell Transplantation, vol. 22, pp. 1171-1183, 2013.
Newman R. E. et al., Treatment of Inflammatory Diseases with Mesenchymal Stem Cells., Inflammation & Allergy—Drug Targets, 2009, vol. 8, pp. 110-123.
Li T.S. et al., Effect of Bone Marrow Mesenchymal Stem Cells on Satellite Cell Proliferation and Apotosis in Immobilization-Induced Muscle Atrophy in Rats., Medical Science Monitor, 2016; vol. 22, pp. 4651-4660.
Colter, D. C., Sekiya, I. & Prockop, D. J. Identification of a subpopulation of rapidly self-renewing and multipotential adult stem cells in colonies of human marrow stromal cells. Proc Natl Acad Sci. 2001;98:7841-7845.
Sekiya I., Muneta T., Horie M. & Koga H. Arthroscopic Transplantation of Synovial Stem Cells Improves Clinical Outcomes in Knees With Cartilage Defects. Clin Orthop Relat Res. 2015;473:2316-26.
Salem, H. K. & Thiemermann, C. Mesenchymal stromal cells: current understanding and clinical status. 2010;28:585-596.

(Continued)

*Primary Examiner* — Teresa E Knight
(74) *Attorney, Agent, or Firm* — Knobbe, Martens, Olson & Bear LLP

(57) ABSTRACT

A method for purifying and enriching mesenchymal stem cells (MSCs) simply and efficiently. Separation of cells expressing CD73 protein on the surface from fresh tissue isolated from a living body allows purification and enrichment of MSCs easily and efficiently. MSCs may be selectively isolated with a single antibody before culturing to establish a culture system of mesenchymal stem cells that enhances the engraftment efficiency in the transplanted site.

11 Claims, 14 Drawing Sheets

(56) References Cited

OTHER PUBLICATIONS

De Bari, C., Dell'Accio, F., Tylzanowski, P. & Luyten, F. P. Multipotent mesenchymal stem cells from adult human synovial membrane. Arthritis Rheum.2001;44: 1928-1942.

Harting, M., Jimenez, F., Pati, S., Baumgartner, J. & Cox, C., Jr. Immunophenotype characterization of rat mesenchymal stromal cells. Cytotherapy. 2008;10:243-253.

Guanerio J., Coltella N., Ala U., Tonon G., Pandolfi PP. & Bernardi R. Bone Marrow Endosteal Mesenchymal Progenitors Depend on HIF Factors for Maintenance and Regulation of Hematopoiesis. Stem Cell Reports. 2014;2:794-809.

Mabuchi, Y. et al., LNGFR(+)THY-1(+)VCAM-1(hi+) cells reveal functionally distinct subpopulations in mesenchymal stem cells. Stem Cell Reports. 2013;1:152-165.

Morikawa, S. et al., Prospective identification, isolation, and systemic transplantation of multipotent mesenchymal stem cells in murine bone marrow. J Exp Med. 2009;206:2483-2496.

International Prelominary Report on Patentability in International Application No. PCT/JP2018/018351, dated Nov. 14, 2019.

Barry. F et al., "The SH-3 and SH-4 Antibodies Recognize Distinct Epitopes on CD73 fromn Human Mesenchymal Stem Cells", Biochemical and Biophysical Research Communications, vol. 289, No. 2, Nov. 1, 2001, pp. 519-524.

Boxall, S et al., "Markers for Characterization of Bone Marrow Multipotential Stromal Cells", Stem Cells International, vol. 19, No. 5, Jan. 1, 2012, pp. 408-412.

Chen, X et al, "CD73 Pathway Contributes to the Immunosuppressive Ability of Mesenchymal Stem Cells in Intraocular Autoimmune Responses", Stem Cells and Development, vol. 25, No. 4, Feb. 15, 2016, pp. 337-346.

Florian, H et al, Journal of Anatomy., vol. 214, No. 5, May 1, 2009, pp. 759-767.

Harichandan, A et al., Best Practice & Research Clinical Haematology, vol. 24, No. 1, Jan. 1, 2011, pp. 25-36.

Kezhe, T. et al, "CD73 Expression on Mesenchymal Stem Cells Dictates the Reparative Properties via its Anti-Inflammatory Activity", Stem Cells International, vol. 2019, May 2, 2019, pp. 1-12.

Extended European Search Report in European Patent Application No. 18798420.8, dated Mar. 3, 2021 in 9 pages.

Office Action in Japanese Patent Application No. 2019-517719; dated May 10, 2022.

Office Action issued in corresponding Japanese Patent Application No. 2019-517719, dated Dec. 6, 2022.

* cited by examiner

METHOD FOR PURIFYING MESENCHYMAL STEM CELLS TO IMPROVE TRANSPLANTATION EFFICIENCY

CROSS-REFERENCE TO RELATED APPLICATIONS

The present application is an application claiming priority to JP 2017-095216 (filing date: May 12, 2017), which is incorporated herein by reference in its entirety.

TECHNICAL FIELD

The present invention relates to a method of isolating, purifying or enriching mesenchymal stem cells. More specifically, it relates to a method of isolating, purifying or enriching mesenchymal stem cells from a fresh tissue isolated from a living organism, using the cell surface expression of a marker protein as an indicator. The present invention also relates to a method for producing mesenchymal stem cells, which can be used for cell transplantation, and a kit for use in such a method.

BACKGROUND ART

Mesenchymal stem cells are somatic stem cells present in the bone marrow, synovium, fat, and umbilical cord; and they have been reported to have the ability to differentiate into cartilage, bone, fat, and nerve cells (Non-patent Document 1). Since they can also be separated from adult tissues, they are used for regenerative therapy of the damaged area in menisci and cartilages (Non-patent Document 2). However, these transplanted cells are expanded by culturing a heterogeneous cell population collected from a tissue, and they are mixed with other cells that make up the tissue besides mesenchymal stem cells.

Recently, it has been reported that mesenchymal stem cells not only can regenerate tissues, but also have an effect of inducing immune tolerance when transplanted simultaneously at hematopoietic cell transplantation (Non-patent Document 3). It is concerned that the effect is attenuated due to mixing of assorted cells besides mesenchymal stem cells.

As a method of evaluating mesenchymal stem cells, the level of cell proliferation and cell surface antigen expressions after culturing were analyzed (Non-patent Documents 4 and 5). However, it was elucidated that assorted cells contained among the bone marrow cells other than mesenchymal stem cells also proliferate, and further, that cells other than mesenchymal stem cells express the mesenchymal cell-like antigen by culturing (Non-patent Document 6).

A system for selectively separating human and mouse mesenchymal stem cells before culturing using multiple surface markers has been established (Non-patent Documents 7 and 8). However, antibodies specific for LNGFR (CD271) and THY-1 (CD90) (Patent Document 1, Non-patent Document 7) are used for the separation of human mesenchymal stem cells, and antibodies specific for PDGFRα (CD140a) and Sca-1 (Non-patent Document 8) are used for the separation of murine mesenchymal stem cells. Different antibodies are used for different species.

CITATION LIST

Patent Documents

Patent Document 1: Japanese Patent Application Kokai Publication No. (JP-A) 2009-60840 (unexamined, published Japanese patent application)

Non-Patent Documents

Non-patent Document 1: Colter, D. C., Sekiya, I. & Prockop, D. J. Identification of a subpopulation of rapidly self-renewing and multipotential adult stem cells in colonies of human marrow stromal cells. Proc Natl Acad Sci. 2001; 98:7841-7845.
Non-patent Document 2: Sekiya I., Muneta T., Horie M. & Koga H. Arthroscopic Transplantation of Synovial Stem Cells Improves Clinical Outcomes in Knees With Cartilage Defects. Clin Orthop Relat Res. 2015; 473:2316-26.
Non-patent Document 3: Salem, H. K. & Thiemermann, C. Mesenchymal stromal cells: current understanding and clinical status. 2010; 28:585-596.
Non-patent Document 4: De Bari, C., Dell'Accio, F., Tylzanowski, P. & Luyten, F. P. Multipotent mesenchymal stem cells from adult human synovial membrane. Arthritis Rheum. 2001; 44: 1928-1942.
Non-patent Document 5: Harting, M., Jimenez, F., Pati, S., Baumgartner, J. & Cox, C., Jr. Immunophenotype characterization of rat mesenchymal stromal cells. Cytotherapy. 2008; 10:243-253.
Non-patent Document 6: Guanerio J., Coltella N., Ala U., Tonon G., Pandolfi P P. & Bernardi R. Bone Marrow Endosteal Mesenchymal Progenitors Depend on HIF Factors for Maintenance and Regulation of Hematopoiesis. Stem Cell Reports. 2014; 2:794-809.
Non-patent Document 7: Mabuchi, Y. et al. LNGFR(+)THY-1(+)VCAM-1(hi+) cells reveal functionally distinct subpopulations in mesenchymal stem cells. Stem Cell Reports. 2013; 1:152-165.
Non-patent Document 8: Morikawa, S. et al. Prospective identification, isolation, and systemic transplantation of multipotent mesenchymal stem cells in murine bone marrow. J Exp Med. 2009; 206:2483-2496.

SUMMARY OF THE INVENTION

Problems to be Solved by the Invention

One of the objectives of the present invention is to provide a method for conveniently isolating, purifying or enriching mesenchymal stem cells (MSCs) of mammals including humans. Another objective of the present invention is to provide a method for producing mesenchymal stem cells, which can be used for cell transplantation, and a kit for use in such a method.

Means for Solving the Problems

The present inventors have found that mesenchymal stem cells (MSCs) can be simply and efficiently purified and enriched by separating cells expressing the CD73 protein on their surfaces from a fresh tissue isolated from a living organism. By the present invention, it is possible to establish a culture system of mesenchymal stem cells that selectively separates, before culturing, only mesenchymal stem cells with a single antibody, increasing the engraftment efficiency to the transplantation site. By the present invention which discovered that the same antigen is recognized across different animal species, it becomes possible to evaluate the safety and efficacy in non-clinical trials using cells expressing the same antigen, and stable transplantation effects are expected by using fresh purified cells rather than assorted cell populations.

The present invention is based on such findings and encompasses the embodiments below.

Embodiment 1

A method for purifying mesenchymal stem cells (MSCs), comprising:
i) preparing a population of fresh cells isolated from a living organism, and
ii) isolating cells that express the CD73 protein on their surfaces.

Embodiment 2

The method according to embodiment 1, wherein the CD73 protein is used as the sole positive selection marker.

Embodiment 3

The method according to embodiment 1 or 2, wherein neither CD29, CD44, CD90, CD271, CD140a nor the leptin receptor is used as a selection marker for purifying MSCs.

Embodiment 4

The method according to embodiments 1-3, further comprising removing blood cells/endothelial cells.

Embodiment 5

The method according to embodiment 4, wherein the blood cells/endothelial cells are removed using CD31, CD45, GPAs, and/or Ter119 as negative selection markers for removal of blood cells/endothelial cells.

Embodiment 6

The method according to embodiments 1-5, wherein the CD73 protein is used as the sole selection marker for MSC purification.

Embodiment 7

The method according to embodiments 1-6, wherein the population of fresh cells isolated from a living organism is derived from bone marrow, adipose tissue, umbilical cord, placenta, synovium, or dental pulp.

Embodiment 8

The method according to embodiments 1-7, further comprising treating a population of fresh cells isolated from a living organism with collagenase.

Embodiment 9

The method according to embodiments 1-6, wherein the population of fresh cells isolated from a living organism is derived from peripheral blood.

Embodiment 10

The method according to embodiments 1-9, wherein the population of fresh cells isolated from a living organism is isolated from the living organism after G-CSF, GM-CSF or AM3100 (prelixafol) is administered to the living organism.

Embodiment 11

The method according to embodiments 1-10, wherein cells expressing the CD73 protein are isolated using a carrier conjugated to the anti-CD73 antibody or FACS.

Embodiment 12

The method according to embodiment 11, wherein the carrier conjugated to the anti-CD73 antibody is a magnetic bead.

Embodiment 13

The method according to embodiment 11, wherein the carrier conjugated to the anti-CD73 antibody is loaded into a column.

Embodiment 14

A method for purifying human mesenchymal stem cells (hMSC), comprising:
i) preparing a population of fresh cells isolated from a living organism; and
ii) isolating cells that express the CD73 protein on their surfaces using a carrier conjugated to the anti-CD73 antibody,
wherein the CD73 protein is used as the sole positive selection marker,
wherein none of CD29, CD44, CD90, CD271 and CD140a and the leptin receptor is used as a selection marker, and
wherein cell adhesion culture is not performed prior to isolating cells that express the CD73 protein on their surfaces.

Embodiment 15

A method of manufacturing mesenchymal stem cells (MSCs) for transplantation, comprising:
i) preparing a population of fresh cells isolated from a living organism;
ii) isolating cells that express the CD73 protein on their surfaces; and
iii) propagating the cells isolated in step ii.

Embodiment 16

A method of manufacturing cells for transplantation, comprising:
i) preparing a population of fresh cells isolated from a living organism;
ii) isolating cells that express the CD73 protein on their surfaces; and
iii) inducing differentiation of the cells isolated in step ii.

Embodiment 17

The methods according to embodiments 1-16, wherein a GMP grade antibody is used.

Embodiment 18

A kit for use in the methods according to embodiments 1-16, comprising a carrier conjugated to the anti-CD73 antibody.

Embodiment 19

The kit according to embodiment 18, wherein the carrier conjugated to the anti-CD73 antibody is a magnetic bead.

Embodiment 20

The kit according to embodiment 18, wherein the carrier conjugated to the anti-CD73 antibody is loaded into a column.

Embodiment 21

A kit for use in the methods according to embodiments 1-16, comprising a label-conjugated anti-CD73 antibody.

Embodiment 22

The kit according to embodiments 18-21, wherein a GMP grade antibody is used.

Embodiment 23

A cell composition comprising cells obtained by the methods according to embodiments 1-16.

Embodiment 24

A method of manufacturing a $CD73^+$ cell composition, comprising:
i) preparing a population of fresh cells isolated from a living organism, and
ii) isolating cells that express the CD73 protein on their surfaces.

Embodiment 25

A method of manufacturing a $CD73^+$ cell composition, further comprising growing the cells isolated in step ii.

Embodiment 26

The method according to embodiment 24 or 25, wherein the CD73 protein is used as the sole selection marker.

Embodiment 27

The method according to embodiments 24-26, wherein cell adhesion culture is not performed prior to isolating cells that express the CD73 protein on their surfaces.

Embodiment 28

The method according to embodiments 24-27, wherein the method does not comprise removing blood cells/endothelial cells prior to isolating cells that express the CD73 protein on their surfaces.

Embodiment 29

The method according to embodiments 24-28, wherein the population of fresh cells isolated from a living organism is derived from bone marrow, subcutaneous fat, visceral fat, villus, chorion, or amnion.

Embodiment 30

The method according to embodiments 24-29, wherein FACS is used to isolate cells that express the CD73 protein on their surfaces.

Embodiment 31

The method according to embodiments 24-30, wherein a GMP grade antibody is used.

Embodiment 32

A method of manufacturing a CD73 cell composition, comprising:
i) preparing a population of fresh cells isolated from a living organism, and
ii) isolating cells that express the CD73 protein on their surfaces using FACS, wherein the population of cells isolated from the living organism is derived from subcutaneous or visceral fat,
wherein the CD73 protein is used as the sole selection marker, and
wherein cell adhesion culture is not performed prior to isolating cells that express the CD73 protein on their surfaces.

Embodiment 33

A $CD73^+$ cell composition obtained by the methods according to embodiments 24-32.

Embodiment 34

The $CD73^+$ cell composition according to embodiment 33, wherein the $CD73^+$ cell purity is at least 90%.

Embodiment 35

The $CD73^+$ cell composition according to embodiment 33 or 34, comprising at least $10^3$ $CD73^+$ cells.

Embodiment 36

A composition for improving transplantation efficiency comprising the $CD73^+$ cell composition according to embodiments 33-35.

Embodiment 37

An anti-inflammatory composition, comprising the $CD73^+$ cell composition according to embodiments 33-35.

Embodiment 38

An immunosuppressive composition, comprising the $CD73^+$ cell composition according to embodiments 33-35.

Embodiment 39

A composition for use in the treatment of a muscle injury or muscle disorder, comprising the CD73+ cell composition according to embodiments 33-35 and muscle satellite cells.

Embodiment 40

A composition for use in the treatment of an inflammatory bowel disease, comprising the CD73+ cell composition according to embodiments 33-35.

Embodiment 41

A composition for use in the treatment or prevention of GVHD, comprising the CD73+ cell composition according to embodiments 33-35.

Embodiment 42

A method for enhancing the efficiency of cell therapy, comprising administering the CD73+ cell composition according to embodiments 33-35 concurrently with allogeneic cells in a cell therapy using allogeneic cells.

Embodiment 43

The CD73+ cell composition according to embodiments 33-35 for co-administration with allogeneic cells in a cell therapy using allogeneic cells to enhance cell therapy efficiency.

MODE FOR CARRYING OUT THE INVENTION

Figure 1:
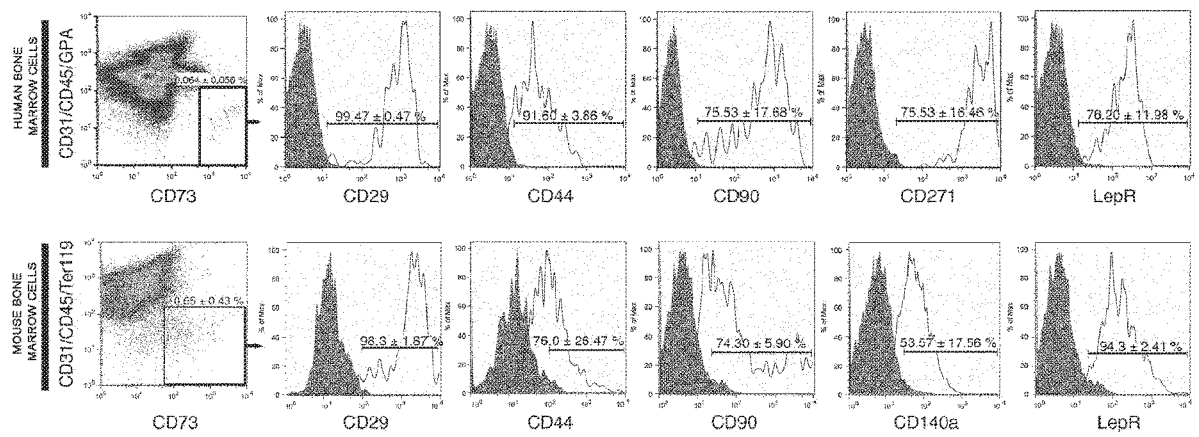
FIG. 1 is a figure showing that CD73+ cells in human and murine bone marrow express mesenchymal stem cell markers.

As discussed above, the present inventors have found that mesenchymal stem cells (MSCs) can be simply and efficiently purified and enriched by separating cells expressing the CD73 protein on their surfaces from fresh tissues isolated from a living organism. The present invention is described in detail below.

Mesenchymal Stem Cells (MSCs)

Mesenchymal stem cells (MSCs) are pluripotent adult stem cells present in multiple tissues such as the umbilical cord, bone marrow, and adipose tissue. Mesenchymal stem cells (MSCs) are rare cells, but they are estimated to exist in the bone marrow at a ratio of 1 per 10,000 to 100,000 nucleated bone marrow cells. Mesenchymal stem cells (MSCs) have self-renewal ability and can differentiate into various cell types such as osteoblasts (osteocytes), chondrocytes, muscle cells, and adipocytes, and therefore their application to regenerative medicine is expected.

According to the definition in Dominici et al. (Minimal criteria for defining multipotent mesenchymal stromal cells. The International Society for Cellular Therapy position statement. Cytotherapy. 2006; 8(4):315-7.), mesenchymal stem cells (MSCs) are cells that (1) adhere to plastic culture dishes, (2) use CD105 (endoglin), CD73 (ecto-5'-nucleotidase), and CD90 (Thy-1) as positive markers, and CD45, CD34, CD14, CD11b, CD79α, and CD19, HLA-Class II (DR) as negative markers, and (3) have the ability to differentiate into bone, fat, and cartilage. Conventional methods for isolating mesenchymal stem cells take advantage of the MSCs' property of adhering to plastic culture dishes to grow.

In order to be identified as MSCs, more than 95% of the cultured cell population must express CD73, CD90 and CD105, and be negative (≤2% positive cells) for CD11b or CD14, CD34, CD45, CD19 or CD79α, and HLA-DR. However, it should be noted that these antigenic profiles are revealed after the cells are cultured in an artificial environment.

As described above, mesenchymal stem cells are often isolated by growing cells attached to culture dishes after long-term culture of cells obtained from tissues such as bone marrow. However, the quality of the stem cells ultimately obtained varies due to the heterogeneity of the cells contained in the starting material. Therefore, techniques for isolating mesenchymal stem cells using surface antigen markers have been developed; and for example, Ogata et al. has shown that human MSCs can be purified using two cell surface markers, LNGFR and THY-1 (Ogata et al., PLoS One. 2015 Jun. 8; 10(6):e0129096.).

CD73 (Ecto-5′-Nucleotidase)

CD73 is an enzyme also called ecto-5′-nucleotidase, and generally has the function of converting AMP to adenosine. Traditionally, CD73 has been included as one of the MSC-defining positive markers. However, until now, it has not been known that MSCs can be isolated using the CD73 expression alone as an indicator. The present inventors have unexpectedly and surprisingly found that MSCs in humans, mice and rats can be substantially purified using the expression of CD73 alone as an indicator.

Purification Method

One embodiment of the present invention relates to a method for purifying mesenchymal stem cells (MSCs), comprising: i) preparing a population of fresh cells isolated from a living organism, and ii) isolating cells that express the CD73 protein on their surfaces. Here, fresh cells are defined as cells that have not undergone a culturing process immediately after being isolated from a living organism; however, fresh cells may be frozen and stored immediately after being isolated from a living organism. In the context of the detailed description of the invention herein, the MSC purification method can also be regarded as a method for isolating or enriching MSCs. The population of cells treated by the method of the present disclosure has at least a 10% increase in the proportion of MSCs in the cell population compared to the population of cells prior to treatment. The process of isolating cells expressing the CD73 protein on their surfaces may be performed in vitro or ex vivo; and flow cytometric sorting (FACS), affinity chromatography, immunopanning, separation using carriers such as magnetic beads can be used, although the selection methods are not limited thereto.

The methods described herein for MSC purification are, in other words, methods for purifying, isolating, or enriching CD73$^+$ cells. In addition, the cell purification methods according to the disclosure herein are sometimes referred to as "fresh purification methods".

In the context of the detailed description of the invention herein, the process of preparing a population of fresh cells isolated from a living organism is considered not to involve a surgical process of isolating tissues from a human body. One embodiment of the present invention may further include isolating a population of fresh cells (tissue) from a living organism.

One embodiment of the present invention relates to a method characterized in using the CD73 protein as the sole positive selection marker. That is, none of CD29, CD44, CD90, CD271, CD140a and the leptin receptor, which are used as markers for identifying cultured cells as MSCs, is used as a positive selection marker for purifying MSCs. In one embodiment of the present invention, none of CD29, CD44, CD90, CD271, CD140a and the leptin receptor is neither used as a selection marker nor as a negative selection marker. In one embodiment of the present invention, the CD73 protein is used as the sole selection marker for MSC purification.

In some embodiments of the present invention, one or more cell-surface markers selected from CD235a, CD45, CD11b, CD105, CD90, CD10, CD140b, CD14, CD19, CD79α, CD34, CD45, HLA-DR, CD31, and GPA are also not used as selection markers.

Since a single marker is used as an indicator for selection, the method according to such an embodiment may be regarded as having a large cost advantage compared to methods using multiple antibodies. This standpoint is particularly important in situations where the use of GMP grade antibodies is required. In addition, the use of expensive multicolor FACS systems is not required, and simple isolation using carriers such as magnetic beads is also feasible.

One embodiment of the present invention relates to a method of using CD31, CD45, GPA, and/or Ter119 as negative selection markers for removing blood cells/endothelial cells. As discussed below, when FACS is used to purify cells, these negative selection markers can readily increase the cell purity.

The cell source in preparing fresh cells isolated from living organisms includes, for example, mammalian bone marrow, umbilical cord, umbilical cord blood, peripheral blood, synovium, adipose tissue, and such. One preferred cell source is bone marrow, but the bone marrow can be bone marrow of spine, sternum, rib, femur, tibia, ilium, and such. Mammals include, but are not limited to, humans, mice, rats. The MSC purification methods using CD73 as an indicator have the advantage of being universally applicable to humans, mice and rats. Preferably, the purification methods of the present disclosure are utilized for purifying human mesenchymal stem cells (hMSCs).

The cell source in preparing fresh cells isolated from living organisms include visceral fat, subcutaneous fat, amnion, chorion, and villus in addition to those described above. Adipose tissues such as subcutaneous fat and visceral fat have the advantage of being relatively easy to obtain. Also, villus can be obtained in considerable quantities (nearly up to 500 g from a pregnant woman), and thus can be a good source for obtaining cells.

When preparing target cells from a tissue isolated from a living organism, the tissue material can be physically processed by pipetting or chemically processed by enzymes to dissociate mesenchymal stem cells contained in the tissue from other cells. For the enzyme, commonly used enzymes such as trypsin and collagenase can be used, but collagenase treatment is preferred. More specifically, the cells are treated with, for example, 0.2% collagenase solution at 37° C. for one hour. When cells are obtained from peripheral blood, it is desirable to hemolyze the erythrocytes in the material in advance, for example, by treating the material with a hypotonic solution. When obtaining cells, one may use a population of cells isolated from a living organism after administering G-CSF, GM-CSF or AM3100 (prelixafol) to the organism.

If the tissue isolated from the organism contains blood cells, the cells may be sorted out using the cell surface expressions of the CD45 and CD235a proteins, but the surface markers are not limited thereto, and for example, the CD31 protein can also be used. Selection methods include, but are not limited to, flow cytometry using fluorescently labeled antibodies, magnetic beads, immunopanning, and affinity chromatography. The sorting of CD45$^-$CD235a$^-$ cells or such may be performed either prior to MSC isolation (purification, enrichment), concurrently with, or after MSC isolation (purification, enrichment). In addition, when preparing the cells of interest from the tissue isolated from a living organism, the dead cells may be removed in advance by reacting the cell population with a dead cell-staining fluorescent dye such as propidium iodide (PI) and removing the fluorescence-stained cells.

One embodiment of the present invention relates to a method for purifying mesenchymal stem cells (MSCs), comprising removing blood cells/endothelial cells. The purification method in this embodiment, for example, comprises: i) preparing a population of fresh cells isolated from a living organism, ii) removing blood cells/endothelial cells, and iii) isolating cells that express the CD73 protein on their surfaces. More specifically, blood cells/endothelial cells can be removed using CD31, CD45, GPAs, and/or Ter119 as negative selection markers for removal of blood cells/endothelial cells. In the methods disclosed herein, after removal of blood cells/endothelial cells, the CD73 protein can be used as the sole selection marker for MSC purification to purify mesenchymal stem cells (MSCs).

Antibodies that specifically recognize the CD73 protein, for example, can be used to isolate cells that express the CD73 protein on their surfaces. Antibodies may be labeled with fluorescent dyes such as FITC, PE, and APC. The antibodies that can be used include, for example, as for human CD73 antibodies, clone AD2 (BD Bioscience) and such. The features of the antibody to be used (monoclonal/polyclonal antibody, isotype, full length/fragment, etc.) and the concentration of the antibody may be determined as appropriate by a person skilled in the art, in consideration of the tissue from which the cell is derived, the activity of the antibody, the method of use of the antibody, and such. The amino acid sequences and encoding nucleic acid sequences of the CD73 proteins of mammals including humans, mice, and rats are known, and this information may be used to generate anti-CD73 antibodies. Antibodies that recognize the human, murine, or rat CD73 protein may be identical, or may vary from species to species. When isolated MSCs are used in human regenerative medicine, GMP-grade antibodies are used.

Isolation of cells expressing the CD73 protein on their surfaces can be performed, for example, using flow cytometry (FACS), immunopanning, affinity chromatography, or carriers such as magnetic beads. In the MSC purification method of the present disclosure, as noted above, no adhesion culture method conventionally used in MSC isolation is performed prior to isolating cells expressing the CD73 protein on their surfaces.

In FACS (fluorescence activated cell sorting), cells are sorted by staining with fluorescent antibodies, and measuring and analyzing the fluorescence emitted by individual cells. For example, the BD Bioscience BD FACSAria Cell Sorter can be used as a FACS system. Fluorescently labeled anti-CD73 antibodies are used to screen CD73 cells, but one skilled in the art can appropriately set up a cell sorter. In addition, CD31$^-$CD45$^-$CD235a$^-$ may be added to the conditions for removing blood cells/endothelial cells in CD73$^+$ cell sorting, and the negative selection markers are not limited thereto.

Cells can also be isolated using carriers such as beads (microspheres) with a bound anti-CD73 antibody. The carrier can be a bead, for example, a magnetic bead, but is not limited thereto. Other carriers such as agarose may be used instead of beads, and the beads may be magnetic agarose beads. Various beads (microspheres) are commercially available and can be used in the present invention.

The binding of the antibody to the carrier may be a covalent bond, a hydrogen bond, or such, but it is not particularly limited. Anti-CD73 antibodies need not be directly bound to the carrier, but may be bound indirectly. A linker (e.g., biotin-avidin system) between the antibody and the carrier can facilitate separation of the antibody from the carrier. Cell isolation can also be performed, for example, using a carrier coupled to another antibody that recognizes the anti-CD73 antibody to bind the anti-CD73 antibody to the cell.

When bone-marrow cells are used, prior to isolating cells with a carrier conjugated to an anti-CD73 antibody, Miltenyi™ magnetic bead selection or such may be used to remove CD34$^+$CD133$^+$ cells.

Purification by affinity chromatography can also be performed, by packing the column with a carrier bound to an anti-CD73 antibody and passing the sample through the column.

Method of Manufacturing Mesenchymal Stem Cells (MSCs) for Transplantation

One embodiment of the present invention relates to a method of manufacturing mesenchymal stem cells (MSCs) for transplantation. Such a manufacturing method comprises, for example, i) preparing a population of fresh cells isolated from a living organism, ii) isolating cells that express the CD73 protein on their surfaces, and iii) propagating the cells isolated in step ii. Details of steps i and ii are as described in other parts of the present specification.

In the step of propagating cells isolated in step ii, the MSCs can be cultured using any known method. Mesenchymal stem cell growth media are known to those skilled in the art, and various media are commercially available. Culture conditions and duration can be determined as appropriate by a skilled artisan.

One embodiment of the present invention relates to a cell population or cell composition comprising MSCs produced by the method described above. The present inventors found that cell populations purified by isolating cells expressing the CD73 protein on their surfaces had high engraftment efficiency in the transplantation site. The cell population comprising MSCs of the present invention contains at least 2%, preferably 10% or more, 20% or more, 30% or more, 40% or more, 50% or more, 60% or more, 70% or more, or 80% or more, and more preferably 90% or more MSCs in the cell population. The overall ratio of MSCs can be measured using cell surface markers as an indicator.

Cell populations comprising MSCs produced by the method described above can be used for transplantation into a living organism. Transplantation may target direct regeneration of the defective or damaged tissue, or it may aim for indirect effects of factors secreted by MSCs. For example, MSCs have been shown to have therapeutic potential in patients with acute myocardial infarction, stroke, multiple system atrophy (MSA), graft-versus-host disorder, and spinal cord injury.

As described below, for the purpose of regenerating specific tissues, the MSCs may be induced to differentiate in some way, followed by transplantation. Gene editing techniques can also be used to modify MSCs prior to transplantation.

One embodiment of the present invention relates to a method for treating a disorder or an injury, comprising: i) preparing a population of fresh cells isolated from a living organism; ii) isolating cells expressing the CD73 protein on their surfaces; iii) propagating the cells isolated in step ii; and iv) transplanting the propagated cells into a patient. The injury can be, for example, meniscal injury. One embodiment of the present invention may be, for example, a cell composition for use in the treatment of meniscal injury.

Method of Manufacturing Cells for Transplantation

One embodiment of the present invention relates to a method of manufacturing cells for transplantation. Such a cell manufacturing method comprises, for example, i) preparing a population of fresh cells isolated from a living organism, ii) isolating cells that express the CD73 protein on their surfaces, and iii) inducing differentiation of the cells isolated in step ii. Details of steps i and ii are as described in other parts of the present specification.

The step of inducing differentiation of the cells isolated in step ii may be any method known for induction of MSC differentiation. Mesenchymal stem cells have multi-lineage potential to differentiate into osteoblasts, osteocytes, and adipocytes. Mesenchymal stem cells can also differentiate into chondrocytes, muscle cells, stromal cells, tendon cells, and such, depending on the conditions of induction of differentiation. Methods for inducing differentiation of mesenchymal stem cells are known to those skilled in the art, and various differentiation-inducing media are commercially available. The conditions and period of culturing can be determined as appropriate by a skilled artisan. For example, the chondrocyte induction medium can be purchased and used from LONZA and such.

One embodiment of the present invention relates to a method of treating a disorder or an injury comprising: i) preparing a population of fresh cells isolated from a living organism; ii) isolating cells expressing the CD73 protein on their surfaces; iii) inducing differentiation of cells isolated in step ii; and iv) transplanting the differentiated cells into a patient. The injury can be, for example, meniscal injury. One embodiment of the present invention may be, for example, a cell composition comprising differentiated cells for use in the treatment of meniscal injury.

Kits

One embodiment of the present invention relates to kits for use in the isolation, purification or enrichment of mesenchymal stem cells (MSCs). In one embodiment, the kits comprise an anti-CD73 antibody. The antibody is preferably of GMP grade.

Kits for isolating MSCs by flow cytometry comprise, for example, a fluorescently labeled anti-CD73 antibody, an anti-CD31 antibody, and an anti-CD45 antibody. The kits for flow cytometry may further comprise other antibodies that recognize different markers for removal of blood cells/endothelial cells, and the anti-CD31 antibody and anti-CD45 antibody may be replaced with other antibodies that recognize different markers.

Kits for isolating MSCs using carriers such as beads (microspheres) comprise a carrier conjugated to an anti-CD73 antibody. The binding of the antibody to the carrier may be a covalent bond, a hydrogen bond, or such, without being particularly limited. The anti-CD73 antibody needs not be directly bound to the carrier, but may be indirectly bound. The kits in one embodiment may include, for example, an anti-CD73 antibody and a carrier coupled to another antibody that binds to the anti-CD73 antibody.

The carrier can be a bead, for example, a magnetic bead, but is not limited thereto. Other carriers such as agarose can be used instead of beads, and the beads can be magnetic agarose beads. Various beads (microspheres) are commercially available and can be used in the present invention.

Kits for isolating MSCs using affinity chromatography comprise a column packed with a carrier conjugated to an anti-CD73 antibody. The kits according to one embodiment may include, for example, a buffer for use in eluting the column-bound cells.

$CD73^+$ Cell Compositions

High-purity $CD73^+$ cell populations or cell compositions can be obtained by using the cell purification methods of the present invention. Thus, one embodiment of the present invention relates to a method for manufacturing a $CD73^+$ cell composition. One embodiment of such a manufacturing method comprises, for example, i) preparing a population of fresh cells isolated from a living organism, ii) isolating cells that express the CD73 protein on their surfaces, and optionally iii) propagating the cells isolated in step ii. Details of steps i and ii are as described in other parts of the present specification. The step of propagating cells, for example, comprises culturing the cells for 3 to 30 days or 10 to 20 days, and for example 14 days. The cell compositions obtained by such methods comprise at least $10^3$, for example, at least $10^4$, preferably $10^5$, more preferably $10^6$ or more, and more preferably 10: or more $CD73^+$ cells. There may be mixing of other cells besides $CD73^+$ cells in the cell compositions, but preferably there is a high $CD73^+$ cell purity. The purity of $CD73^+$ cells in the cell compositions is at least 50%, preferably at least 80%, more preferably at least 85%, at least 90%, 95%, 96%, 97%, 98%, or 99%. From the standpoint of increasing purity, it is preferred that cells are separated by FACS. Without particular limitations, the cells contained in the cell composition are preferably human cells. In one embodiment of the present invention, the cell composition comprising $CD73^+$ cells is stored in a single container.

The cell compositions can be used, for example, for transplantation for therapeutic purposes. Cell transplantation can be performed, for example, to regenerate damaged areas, regenerate functionally compromised tissues, or suppress inflammation or immune responses. The subject for transplantation is preferably a human, without particular limitations. One embodiment of the present invention relates to cell compositions comprising at least $10^3$, for example, $10^4$ or more, preferably $10^5$ or more, more preferably $10^6$ or more, and more preferably $10^7$ or more $CD73^+$ cells for use in the treatment of a disorder or an injury. The disorder or injury to be treated includes, but is not limited to, inflammatory diseases, immunologic disorders, autoimmune diseases, collagen disorders, allergic disorders, graft-versus-host disorder (GVHD), inflammatory bowel diseases, ulcerative colitis, Crohn's disease, muscle injuries, muscle ruptures, innate or acquired muscle disorders, muscular dystrophy, congenital myopathy, distal myopathy, myotonic disorders, inflammatory muscle disorders, periodic paralyses, metabolic muscle disorders, myasthenia gravis, congenital myasthenia syndromes, mitochondrial disorders, and sarcopenia. The cell composition may be transplanted together with other cells or tissues.

Compositions for Improving Transplantation Efficiency

One embodiment of the present invention relates to a composition for improving transplantation efficiency or engraftment efficiency of a graft (cell or tissue), which comprises a $CD73^+$ cell composition of the present invention. When cells or tissues are transplanted into a living organism, normally other cells cannot survive after transplantation unless immunosuppressive agents are administered. The present inventors have surprisingly found that by co-administering allogeneic (derived from the same mouse species as that of skeletal muscle satellite cells) $CD73^+$ cells, allogeneic skeletal muscle satellite cells can be engrafted as regenerative muscle. Co-administration of $CD73^+$ cells inhibits the infiltration of inflammatory cells into the transplantation site. Thus, one of ordinary skill in the art understands that transplantation of $CD73^+$ cells with a graft (cells or tissue) of interest can increase graft survival. One embodiment of the present invention also relates to a method for treating a disorder or an injury, comprising transplanting cells or a tissue of interest together with $CD73^+$ cells. More specifically, one embodiment of the present invention relates to a method for regenerating a muscle tissue, comprising administering a CD73+ cell composition to a subject in need of treatment with muscle satellite cells. In addition, one embodiment of the present invention relates to the use of CD73+ cells to improve the transplantation efficiency or survival rate of the cells or tissue of interest. The preferred grafts (cells or tissues) are allogeneic, but they are not limited thereto, and allogeneic or autologous cells or tissues may be used. CD73+ cells may also be allogeneic, or autologous. A specific clinical state is, for example, graft-versus-host disorder (GVHD: graft versus host disorder).

One embodiment of the present invention also relates to a method for enhancing the cell therapy efficiency in cell therapies that use allogeneic cells, which comprises administering a CD73+ cell composition concurrently with the allogeneic cells. In addition, one embodiment of the present invention relates to a CD73+ cell composition for co-administration with allogeneic cells to increase cell therapy efficiency in cell therapies that use allogeneic cells.

Anti-Inflammatory Compositions

One embodiment of the present invention relates to anti-inflammatory compositions comprising a CD73+ cell composition of the present invention. The present inventors demonstrated that the administration of CD73+ cells improved the disorder state in the murine model of ulcerative colitis. Further, it is shown that the infiltration of inflammatory cells can be suppressed by simultaneously transplanting the CD73+ cells when transplanting muscle satellite cells to the area of muscle injury. Thus, it is understood by those skilled in the art that CD73+ cells can be used to suppress the inflammatory responses in the organism. One embodiment of the present invention also relates to a method of treating inflammatory diseases, comprising administering CD73+ cells to a subject in need of treatment. More specifically, one embodiment of the present invention relates to a method of treating inflammatory bowel diseases (ulcerative colitis, Crohn's disease), which comprise administering a CD73+ cell composition to a subject in need of treatment. In addition, one embodiment of the present invention relates to the use of CD73+ cells in suppressing an inflammatory response or treating an inflammatory disease.

Immunosuppressive Compositions

One embodiment of the present invention relates to immunosuppressive compositions or immune tolerance-inducing compositions comprising a CD73+ cell composition of the invention. The present inventors have surprisingly found that allogeneic (derived from the same mouse species as that of skeletal muscle satellite cells) CD73+ cells, allogeneic skeletal muscle satellite cells can be engrafted as regenerative muscle. When cells or tissues are transplanted into a living organism, normally allogeneic cells cannot be engrafted after transplantation unless immunosuppressive agents are administered. Thus, one skilled in the art understands that CD73+ cells can be used to suppress immune responses of the living organism or to induce immune tolerance. One embodiment of the present invention also relates to an immunosuppressive (immune tolerance-inducing) method comprising administering CD73+ cells to a subject in need of treatment. In addition, one embodiment of the present invention relates to the use of CD73+ cells in suppressing immune responses (inducing immune tolerance) or treating immune diseases.

Hereinbelow, the examples are shown to specifically explain the present invention, without limiting the scope of the present invention thereby. The present inventors investigated the functions of CD73+ cells in human, murine, and rat bone marrow tissues. Cells from the bone marrow tissues were sorted using the CD73 surface antigen as an indicator, and whether the CD73+ cells contain cells showing the mesenchymal stem cell phenotype was verified. Further, efficient engraftment was verified when transplantation to the subcutaneous tissue was carried out. Specific examples are shown below.

EXAMPLES

Example 1: Surface-Antigen Analysis of CD73+ Cells Present in Bone-Marrow Tissues Collection and Preparation of Bone Marrow Cells The materials used were human myelomonocytic cells (Cat. No.: 2M 125C) (20 years old or younger, male), rats (Lewis, 8-10 weeks old, male), and mice (C57BL/6-J, 6-9 weeks old) purchased from LONZA. Frozen human myelomonocytic cells (2M-125C) preserved with liquid nitrogen were removed and incubated in a 37° C. incubator for 1 minute. Then, they were quickly thawed in 9 ml of HBSS(-) solution (Hanks' Balanced Salt Solution) warmed to 37° C. in advance. Centrifugation was performed in a centrifuge (800 g) at room temperature for 5 minutes, and after removal of the supernatant, the cell pellet was resuspended in a fresh HBSS(-) solution to obtain a human myeloid cell suspension.

Rat and mouse bone marrow cells were collected from adult femur, tibia, and ilium. After removal of the outer muscles and connective tissue with nonwoven fabrics, the femur, tibia, and ilium were washed with PBS(-). After a total of 150 to 200 times of cutting with osteotomy scissors (Matsuyoshi Medical General) and surgical scissors (Muromachi Equipment), bone fragments were washed with an HBSS(-) solution to wash out blood cells. The remaining bone fragments were further finely minced and placed in 0.2% collagenase solution (wako) (DMEM) supplemented with 25 U/ml DNase1 (sigma), and shaken at 37° C. for 1 hour at a rate of 100 r/min. Collagenase-treated bone fragments were further minced with scissors, gently crushed with pestles, washed with an HBSS(-) solution, and filtered through a 70-µm mesh cell strainer (Falcon). Centrifugation was performed at 800 g for 5 minutes at 4° C., and after removal of the supernatants, the cell pellets were resuspended in a new HBSS(-) solution to obtain rat and murine myeloid cell suspensions. To remove erythrocytes, cell pellets after centrifugation were subjected to a hemolysis procedure with the ACK solution (LONZA) or water. The bone marrow suspension was obtained by removing fragments of erythrocytes with a cell strainer.

Cell-Surface Antibody Staining

Bone marrow cells ($2.0 \times 10^8$-$4.0 \times 10^8$) obtained by the above procedure were suspended in 1 mL HBSS(-) solution and added to 15 mL centrifuge tubes. One-fold dilutions of the APC- or PE-labeled anti-human CD73 antibody, PE-cy7-labeled anti-CD31 antibody, PE-cy7-labeled anti-CD45 antibody, and PE-cy7-labeled anti-CD235a antibody were suspended in cell suspensions at 2 to 3 µL (antibody quantity: 0.45 to 0.7 µg), and 200 µL was dispensed into tubes. As human mesenchymal stem cell markers, the APC-labeled anti-human CD29 antibody, APC-labeled anti-CD44 antibody, FITC-labeled anti-CD90 antibody, PE-labeled anti-CD271 antibody, and APC-labeled anti-leptin receptor antibody were added to the tubes, and immunostaining was performed on ice for 30 minutes with protection from light (using BD antibodies and R&D antibodies). One-fold dilutions of the APC- or PE-labeled anti-mouse CD73 antibody, PE-cy7-labeled anti-CD31 antibody, PE-cy7-labeled anti- CD45 antibody, and PE-cy7-labeled anti-Ter119 antibody were suspended in cell suspensions and 200 μL was dispensed into tubes. As mouse mesenchymal stem cell markers, the FITC-labeled anti-mouse CD29 antibody, FITC-labeled anti-CD44 antibody, PE-labeled anti-CD90 antibody, APC-labeled anti-CD140a antibody, biotin-labeled anti-leptin receptor antibody, and PE-labeled streptavidin were added into tubes, and immunostaining was performed on ice for 30 minutes with protection from light (using BD antibodies). One-fold dilutions of the APC-labeled anti-rat CD73 antibody, biotin-labeled anti-CD31 antibody, biotin-labeled anti-CD45 antibody, and PEcy7-labeled streptavidin were suspended in cell suspensions, and 200 μL was dispensed into tubes. As rat mesenchymal stem cell markers, the FITC-labeled anti-rat CD29 antibody, PE-labeled anti-CD44 antibody, FITC-labeled anti-CD54 antibody, and BV421-labeled anti-CD90 antibody were added into the tubes, and immunostaining was performed on ice for 30 minutes with protection from light (using BD antibodies). Then, 500 μL of the HBSS(−) solution was added, and the solution was centrifuged at 800 g at 4° C. for 5 minutes. The precipitated cell populations were suspended in 3 mL of propidium iodide (PI)-added HBSS(−) solution at a concentration of 2 μg/mL to prepare about $1 \times 10^7$ cells. For the cell suspension, the cell suspensions obtained using 5 ml mesh round tubes (BD) were used for the flow cytometer analysis below.

Cell-Surface Antigen Analysis of CD73 Cells

Figure 2:
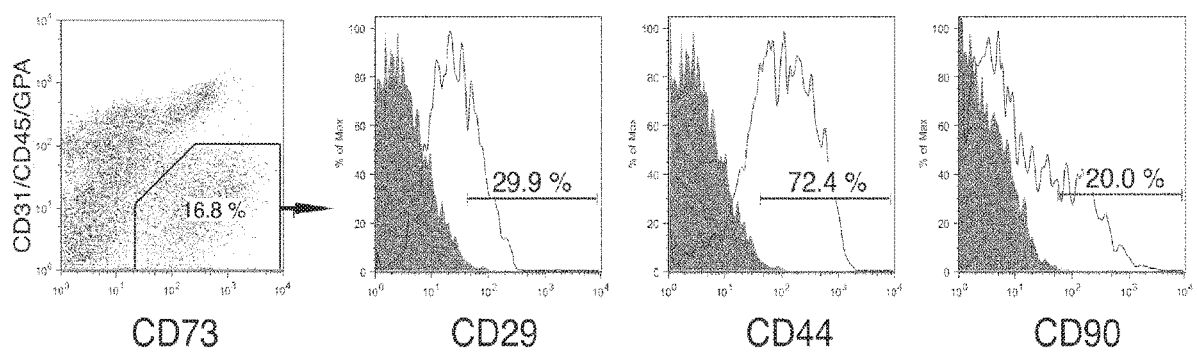
FIG. 2 is a figure illustrating surface-antigen analysis of CD73+ cells in human adipose tissue.
Figure 3:
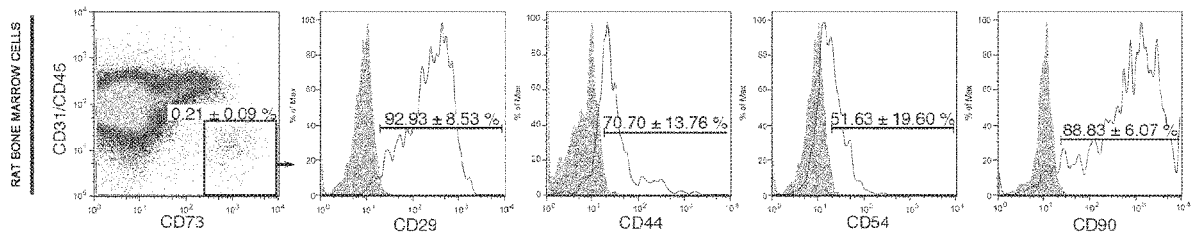
FIG. 3 is a figure showing that CD73+ cells in rat bone marrow express mesenchymal stem cell markers.

Human, mouse and rat bone marrow cells reacted with surface antigen antibodies were analyzed using a flow cytometer. FACSAria was used for the flow cytometer. After the PI-negative cell population, which was a live cell fraction, was gated and doublet cells were gated out, the longitudinal axis was deployed for the blood cell/endothelial marker (human: CD31/CD45/GPA; mouse: CD31/CD45/Ter119; rat: CD31/CD45) and the transverse axis was deployed for the CD73 marker. The expression analysis of mesenchymal stem cell markers in the cell population was carried out by setting the gate for blood cell/endothelial marker-negative and CD73 marker-positive cell population. The results showed that CD73+ cells present in human and mouse bone marrow were all positive for CD29, CD44, CD90, CD271 (human), CD140a (mouse), and the leptin receptor (see FIG. 1, Tables 1 and 2). In addition, CD73+ cells present in a human adipose tissue could also be isolated with the antibody described above (clone AD2), and expressed the mesenchymal stem-cell markers CD29, CD44, CD90 (see FIG. 2). CD73+ cells present in rat bone marrow were mostly positive for CD29, CD44, CD54, CD90 (see FIG. 3 and Table 3).

TABLE 1

| Human protein | | | | |
|---|---|---|---|---|
| CD29 | CD44 | CD90 | CD271 | Leptin receptor |
| Positive cell rate 99.47% | 91.6% | 75.53% | 75.53% | 76.20% |

TABLE 2

| Mouse protein | | | | |
|---|---|---|---|---|
| CD29 | CD44 | CD90 | CD140a | Leptin receptor |
| Positive cell rate 98.3% | 76.0% | 74.3% | 53.57% | 94.3% |

TABLE 3

| Rat protein | | | |
|---|---|---|---|
| CD29 | CD44 | CD90 | CD54 |
| Positive cell rate 92.93% | 70.70% | 88.83% | 51.63% |

Example 2: Analysis of the Colony-Forming Ability of CD73+ Cells Effect of Cell Purification by CD73

The CD73+ cells shown in Example 1 were separated using a flow cytometer. A mesenchymal stem cell growth medium (DMEM+20% FBS+1% penicillin/streptomycin) was added to a 96-well plate at 200 μl, and one cell was sorted per well. The plate was cultured in an incubator at 37° C., and the colonized wells were counted 14 days later.

Figure 4:
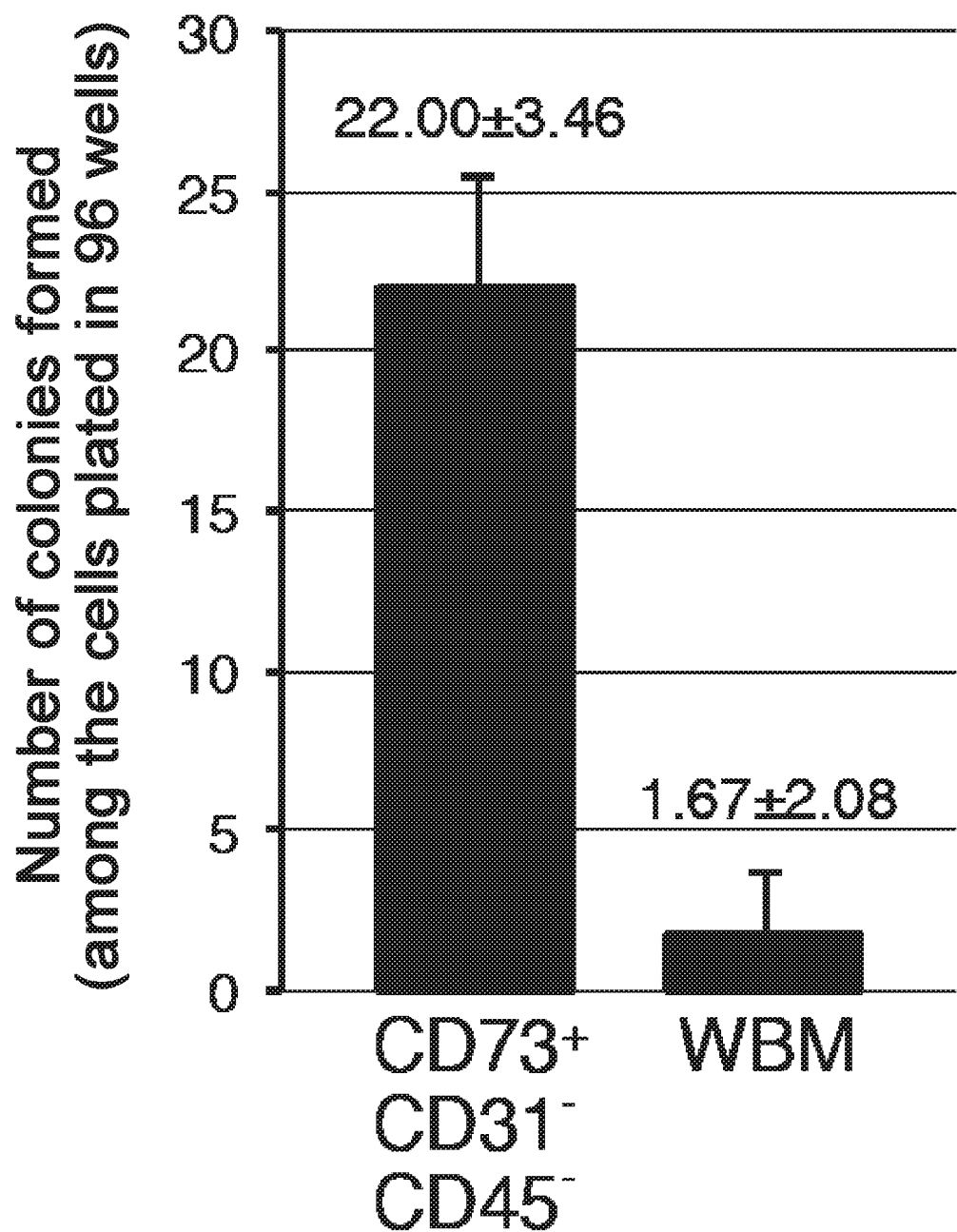
FIG. 4 is a figure showing that a population of fresh cells purified using a CD73 antibody has a high colony-forming ability compared with cells in the whole bone marrow.

The results showed that the colony-forming ability, which is also a feature of mesenchymal stem cells, was 13-fold or higher than the colony-forming ability of the cells in whole bone marrow (Whole Bone Marrow: WBM) (see FIG. 4).

Example 3: Engraftment Function Analysis of CD73+ Cells Evaluation of the Survival Rate by Subcutaneous Transplantation of Mesenchymal Stem Cells The CD73+ cells were separated, and after two passages in the mesenchymal stem cell growth medium, the cells were added into a 15 ml centrifuge tube and centrifuged after the cell number reached $1.0 \times 10^6$-$3.0 \times 10^6$. The pelleted cells were suspended in the chondrocyte induction medium (LONZA)+TGFb3+BMP6, centrifuged at 200 g for 4 minutes, and cultured in a 37° C. incubator. Induction of differentiation was carried out for two weeks, with replacement of fresh chondrocyte induction medium every four days.

The obtained cartilage cell pellet was transplanted to the subcutaneous tissue of the rat head, and the tissue was collected after two weeks to make freeze sections and paraffin embedded sections. The frozen sections were stained with an Iba1 antibody (Wako), which is a macrophage marker, an Aggrecan antibody (obtained from Developmental Studies Hybridoma Bank), which stains the cartilage matrix, and DAPI (Vector), which stains the nuclei of cells. The paraffin sections were stained with safranin O (Muto Pur Chemicals Co.), which stains the cartilage matrix.

Figure 5:
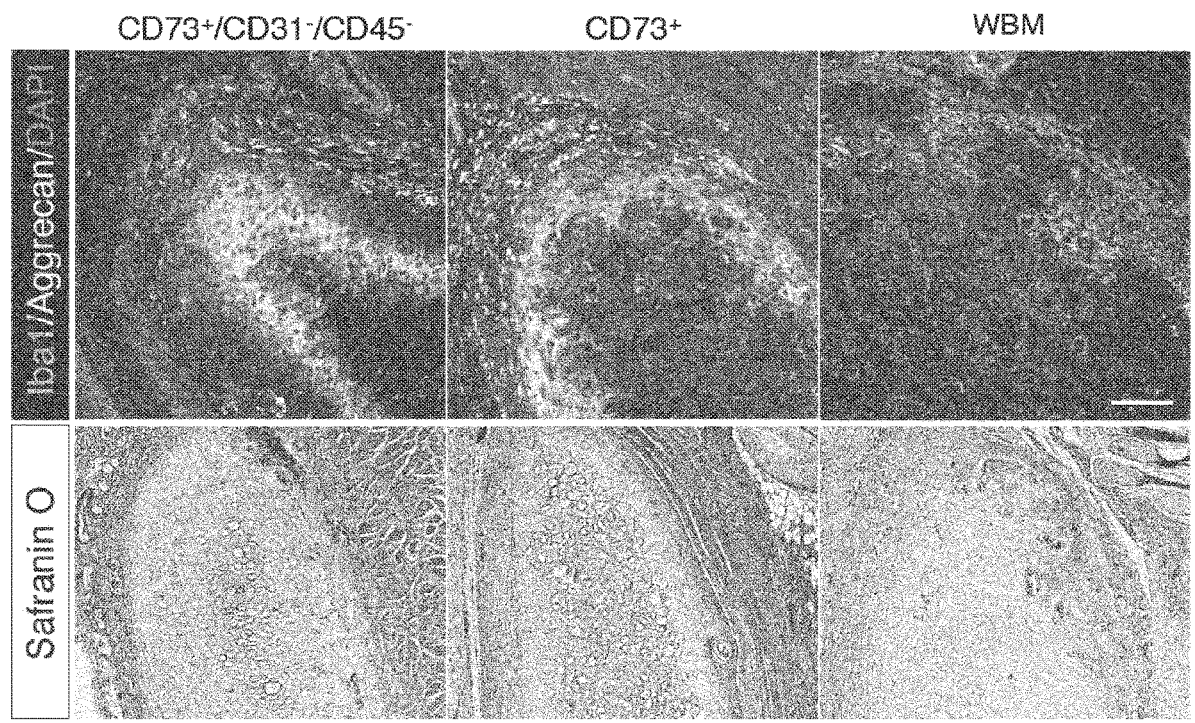
FIG. 5 is a figure showing that a cultured cell population isolated with the CD73 antibody efficiently engrafted in the transplanted site and suppressed the infiltration of macrophages.

As a result of examining the transplanted cells, it was confirmed that for the cell population of purified CD73+ cells, the cartilage-forming ability after the transplantation was high and there was little infiltration of macrophages. On the other hand, whole bone marrow cells cultured without cell purification had reduced cartilage-forming ability, and macrophage infiltration was confirmed (see FIG. 5).

Example 4: Isolation of CD73+ Cells from Human Mesenchymal Tissues

Figure 6:
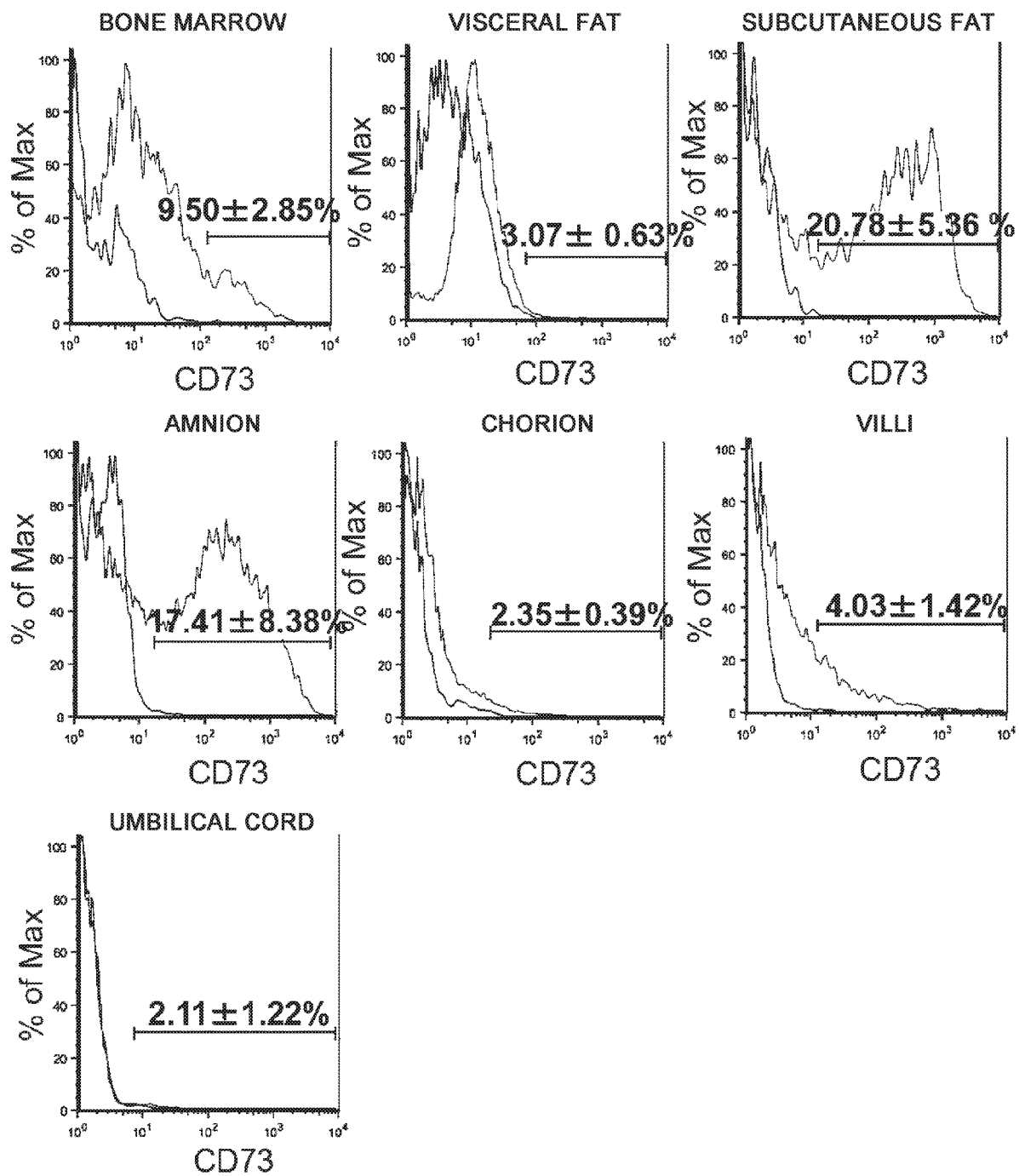
FIG. 6 is a figure showing the results of analyzing the percentage of CD73+ cells in human mesenchymal tissues (bone marrow, visceral fat, subcutaneous fat, amnion, chorion, villus, and umbilical cord).

Bone marrow, visceral fat, subcutaneous fat, amnion, chorion, villus, and umbilical cord were fragmented and treated with 0.2% collagenase solution at 37° C. for one hour. Cells were labeled with an antibody that specifically recognizes the CD73 protein and analyzed by flow cytometry. The results revealed that CD73+ cells were present in 9.5% of the bone marrow, 3.07% of the visceral fat, 20.78% of the subcutaneous fat, 17.41% of the amnion, 2.35% of the chorion, 4.03% of the villus, and 2.11% of the umbilical cord (see FIG. 6).

Example 5: Analysis of the Colony-Forming Ability of CD73+ Cells

Figure 7:
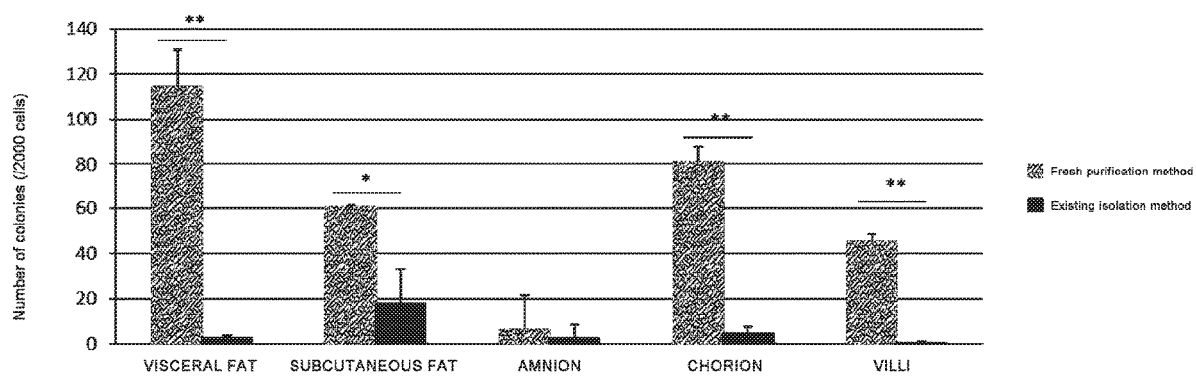
FIG. 7 is a graph illustrating the result of investigating the colony-forming ability of CD73+ cells obtained from bone marrow, visceral fat, subcutaneous fat, amnion, chorion, and villus.
Figure 8:
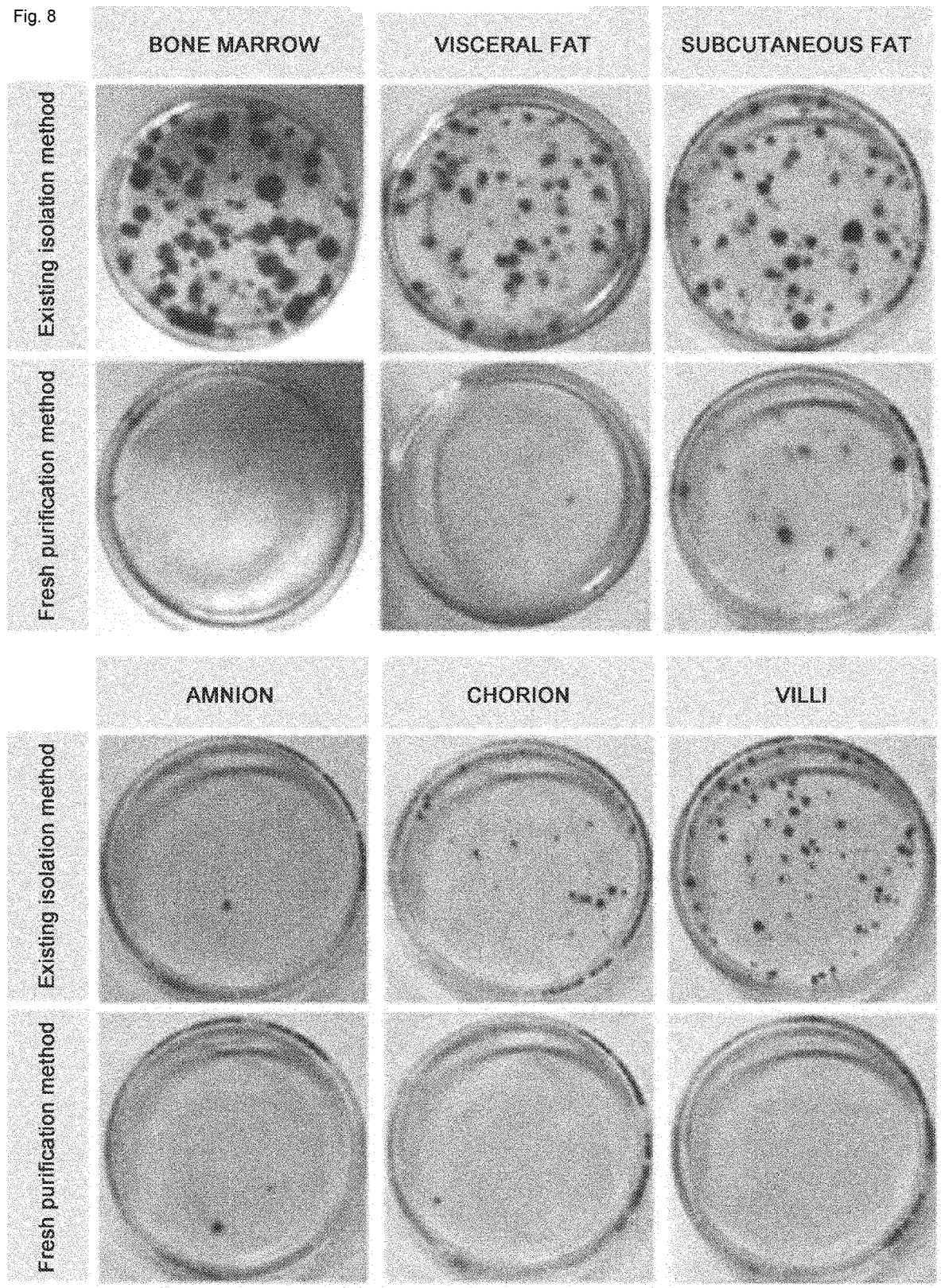
FIG. 8 is a photograph of a culture dish showing the colony-forming ability of CD73+ cells obtained from bone marrow, visceral fat, subcutaneous fat, amnion, chorion, and villus.

The colony-forming ability of CD73+ cells obtained from bone marrow, visceral fat, subcutaneous fat, amnion, chorion, and villus was examined. No CD73+ cells were obtained from the umbilical cord. The results revealed that by the fresh purification method of the present invention, cells with colony-forming ability among CD73+ cells in each of the tissues could be efficiently isolated from bone marrow, visceral fat, subcutaneous fat, chorion, and villus (see FIGS. 7 and 8).

Example 6: Growth Potential Analysis of CD73+ Cells

Figure 9:
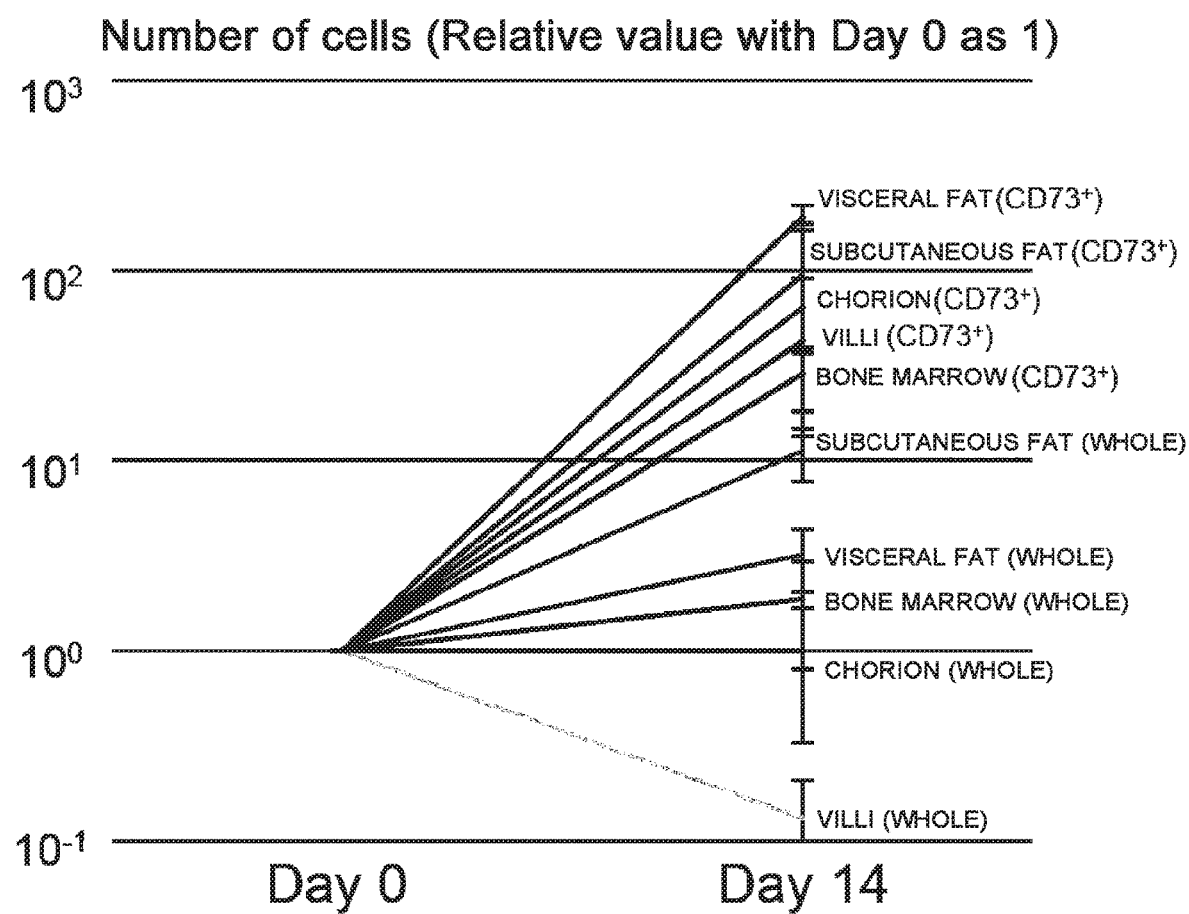
FIG. 9 is a graph illustrating the result of investigating the growth potential of CD73+ cells isolated from subcutaneous fat, visceral fat, chorion, and villus. It shows the relative cell number on the fourteenth day (Day 14) of culturing when the beginning of culturing (Day 0) is set to 1.

The growth potential of CD73 cells isolated from subcutaneous fat, visceral fat, chorion, and villus was examined. The results showed that CD73+ cells isolated from subcutaneous fat, visceral fat, chorion, and villus could be grown in 14 days of culturing, yielding approximately a cell number 100-fold of that before culturing (see FIG. 9). Therefore, the fresh purification in the present invention may reduce the number of administered cells used for transplantation into living organisms compared to conventional methods.

Example 7: Murine Model of Ulcerative Colitis

Figure 10:
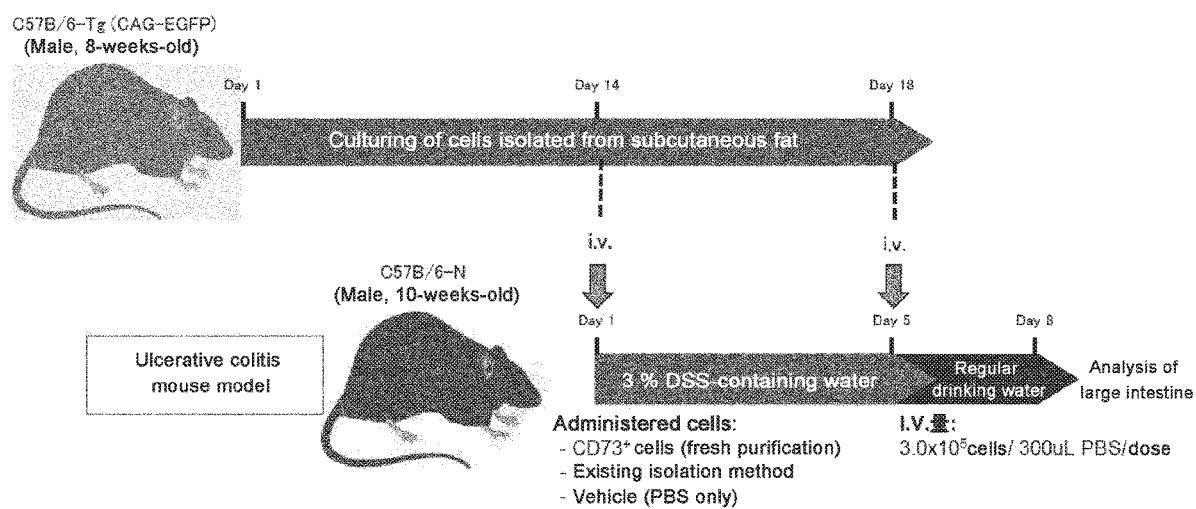
FIG. 10 is a figure illustrating the experimental protocol using a murine model of ulcerative colitis.

Mice with ulcerative colitis induced by administering 3% dextran sulfate sodium (DSS) in drinking water were transplanted with CD73+ cells and MSCs by an existing isolation method (see FIG. 10). More specifically, CD73+ cells were obtained from the subcutaneous adipose of 8-week-old male C57BL/6-Tg (CAG-EGFP) mice, and 10-week-old male C57BL/6-N mice were intravenously administered (I.V.) with vehicle, fresh purified CD73+ cells, or MSCs by an existing isolation method (cells cultured for 14 days or 18 days, respectively) on Days 1 and 5 of 3% DSS administration. Thereafter, DSS administration was discontinued, and the large intestines were examined on Day 8.

Figure 11:
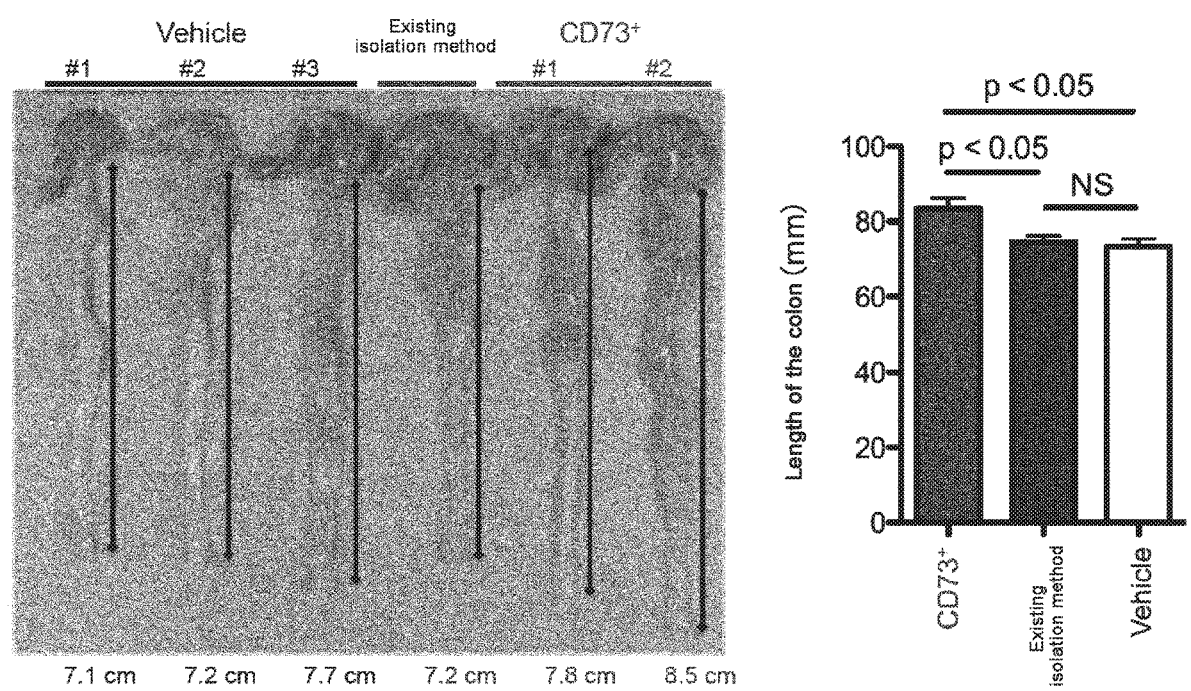
FIG. 11 presents a photograph and graph showing the effects of administering CD73+ cells in a murine model of ulcerative colitis. The left photograph shows the large intestine removed on Day 8 of the experiment. The graph on the right shows the results of analyzing the length of the colon.

It is known that the length of the large intestine is shortened as one of the indicators of ulcerative colitis. As a result, the reduction in colon length was suppressed in the group treated with CD73+ cells, as compared with the vehicle group not treated with the cells and the group treated with MSCs obtained by the existing isolation method (see FIG. 11). It is considered that the administered CD73+ cells stimulated the epithelial cells of the recipient mice themselves to regenerate.

Figure 12:
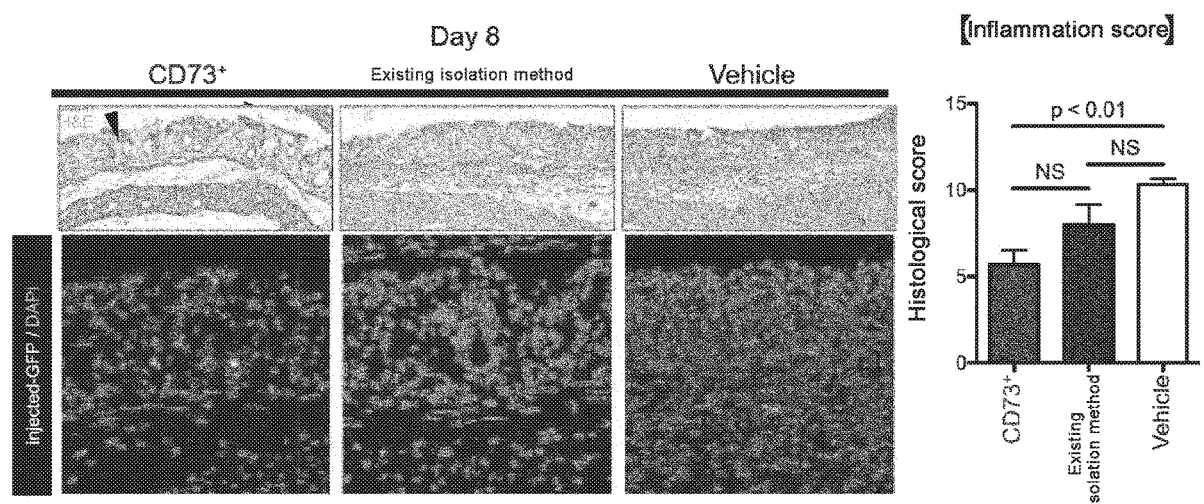
FIG. 12 presents a photograph and graph showing the results of histological examination of the area of rectal inflammation. The photograph on the left shows homing of the transplanted cells to the inflamed area as a result of administering CD73+ cells, and the effect of maintaining the architecture of the large intestine. The graph on the right shows a significantly lower inflammation score in the CD73+ group.

Histological examination of the site of rectal inflammation revealed that as a result of the administration of CD73+ cells, the transplanted cells homed to the site of inflammation, and the architecture of the large intestine was preserved. This was rarely seen in the group that received MSCs of the existing isolation method (see FIG. 12). The inflammation score was also significantly lower in the CD73+ cell group than in the vehicle group (see FIG. 12).

Example 8: Co-Transplantation of Skeletal Muscle Satellite Cells and CD73+ Cells The skeletal muscle stem cells (satellite cells) of allogeneic mice were administered to mice with muscle damage induced by administering cardiotoxin (CTX) to the tibialis anterior muscle. Normally, allogeneic cells cannot survive without immunosuppressive drugs. However, by co-administration of allogeneic (derived from the same mouse species as that of skeletal muscle satellite cells) CD73+ cells, allogeneic skeletal muscle satellite cells can be engrafted as regenerative muscle (see FIGS. 13 and 14).

Figure 13:
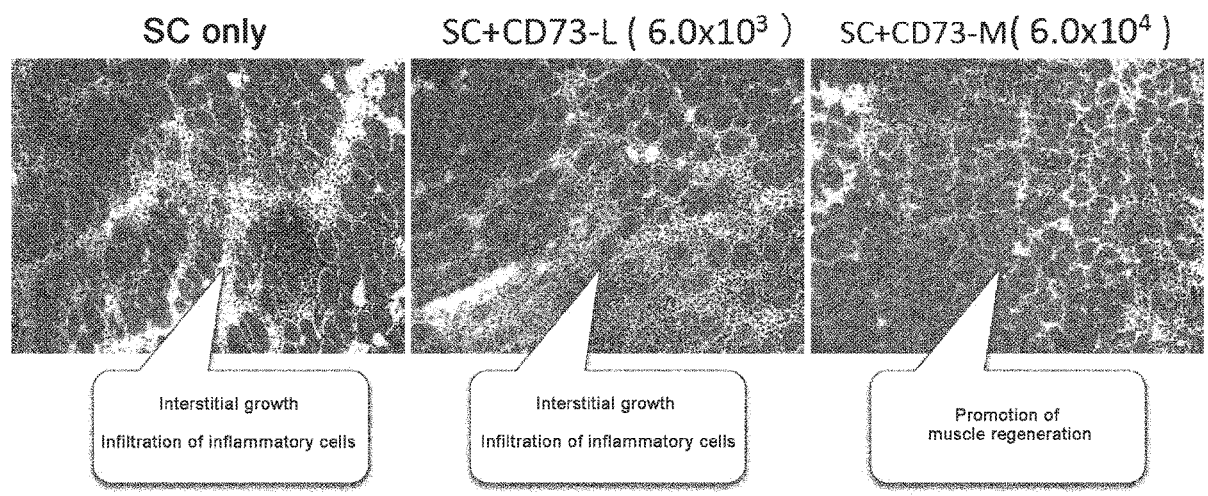
FIG. 13 is an image showing the results of administering skeletal muscle stem cells (satellite cells) of an allogeneic mouse to a mouse with muscle damage induced by administering cardiotoxin (CTX) to the tibialis anterior muscle. Allogeneic CD73+ cells were co-administered.
Figure 14:
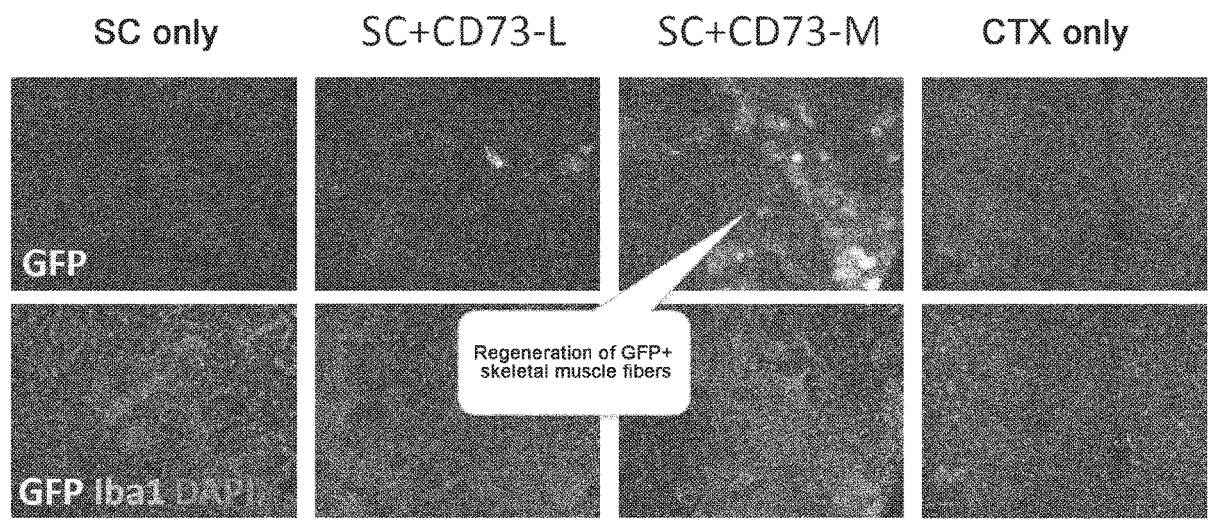
FIG. 14 is an image showing the results of administering skeletal muscle stem cells (satellite cells) of an allogeneic mouse to a mouse with muscle damage induced by administering cardiotoxin (CTX) to the tibialis anterior muscle. Allogeneic CD73+ cells were co-administered.

On the donor side, SM/C-2. 6-positive muscle satellite cells derived from the C57BL/6-Tg (CAG-EGFP) mice and CD73+ cells derived from the 8-week-old male C57BL/6-N mice were used. The muscle satellite cells were cultured in a laminin-containing medium for five days. CD73+ cells were cultured for two weeks. On the recipient side, 8-week-old male BALBcA mice were used. The muscle satellite cells were transplanted at $6.0 \times 10^5$. CD73+ cells were used for transplantation at either $6.0 \times 10^3$ cells (SC+CD73-L) or $6.0 \times 10^4$ cells (SC+CD73-M). Transplantation was performed one day after muscle injury was induced by administering snake venom (CTX), and analysis was performed 14 days after transplantation. As shown in FIGS. 13 and 14, when $6.0 \times 10^4$ of CD73+ cells were transplanted together with muscle satellite cells (SC+CD73-M), cells from allogeneic mice specifically formed regenerative muscle and promoted muscle regeneration.

The present specification shows the preferred embodiments of the present invention, and it is clear to those skilled in the art that such embodiments are provided simply for the purpose of exemplification. A skilled artisan may be able to make various transformations, and add modifications and substitutions without deviating from the present invention. It should be understood that the various alternative embodiments of invention described in the present specification may be used when practicing the present invention. Further, the contents described in all publications referred to in the present specification, including patents and patent application documents, should be construed as being incorporated the same as the contents clearly written in the present specification by their citation.

INDUSTRIAL APPLICABILITY

The present inventors have found that mesenchymal stem cells (MSCs) can be simply and efficiently purified and enriched by separating cells expressing the CD73 protein on their surfaces from fresh tissues isolated from living organisms. By the present invention, it is possible to establish a mesenchymal stem cell culture system which selectively separates only mesenchymal stem cells with a single antibody before culturing, and increases the engraftment efficiency in the transplantation site. Selection with a single antibody offers a large cost advantage over multiple-antibody methods. In addition, since the selection is based on single antibodies, the use of expensive multicolor FACS systems is not required, and isolation using magnetic beads becomes feasible. Furthermore, by the present invention, the same antigen is recognized across different animal species, enabling the evaluation of safety and efficacy in non-clinical studies using cells expressing the same antigen, and thus the stable transplantation effect is expected by using fresh purified cells rather than assorted cell populations.

The invention claimed is:

1. A method for purifying mesenchymal stem cells (MSCs), comprising:
   i) preparing a population of fresh cells isolated from a living organism,
   ii) isolating cells that express the CD73 protein on their surfaces and do not express a single combination of markers selected from the group consisting of CD31/CD45/GPA, CD31/CD45/Ter119, and CD31/CD45 to obtain isolated cells, wherein no other negative or positive selection markers are used to select the cells for isolation.

2. The method according to claim 1, further comprising removing blood cells/endothelial cells.

3. The method according to claim 1, wherein the population of fresh cells isolated from a living organism is derived from bone marrow, adipose tissue, umbilical cord, placenta, synovium, or dental pulp.

4. The method according to claim 1, further comprising treating a population of fresh cells isolated from a living organism with collagenase.

5. The method according to claim 1, wherein the population of fresh cells isolated from a living organism is derived from peripheral blood.

6. The method according to claim 1, wherein the population of fresh cells isolated from a living organism is isolated from the living organism after G-CSF, GM-CSF or AM3100 (prelixafol) is administered to the living organism.

7. The method according to claim 1, wherein cells expressing the CD73 protein on their surfaces are isolated using a carrier conjugated to an anti-CD73 antibody or by FACS.

8. The method according to claim 7, wherein the carrier conjugated to the anti-CD73 antibody is a magnetic bead.

9. The method according to claim 7, wherein the carrier conjugated to the anti-CD73 antibody is loaded into a column.

10. The method according to claim 1,
    wherein cell adhesion culture is not performed prior to isolating cells that express the CD73 protein on their surfaces.

11. A method for purifying mesenchymal stem cells (MSCs), comprising:
    i) preparing a population of fresh cells isolated from a living organism;
    ii) isolating cells that express the CD73 protein on their surfaces, and using $CD73^+$ as the sole selection marker.

* * * * *